United States Patent [19]
Kennedy

[11] Patent Number: 5,718,579
[45] Date of Patent: Feb. 17, 1998

[54] DRILL GUIDE KIT

[76] Inventor: Brent D. Kennedy, 8211 Top of the World Dr., Salt Lake City, Utah 84121

[21] Appl. No.: 567,777

[22] Filed: Dec. 5, 1995

[51] Int. Cl.⁶ .................................................. A61C 3/00
[52] U.S. Cl. ................................................ 433/75; 433/213
[58] Field of Search ............................ 433/215, 75, 173, 433/72, 76, 213

[56] References Cited

U.S. PATENT DOCUMENTS

| | | | |
|---|---|---|---|
| 3,407,503 | 10/1968 | Nealon | 433/76 |
| 4,708,654 | 11/1987 | Branemark | 433/213 |
| 5,064,374 | 11/1991 | Lundgren | 433/213 |
| 5,125,833 | 6/1992 | Berceaux | 433/213 |
| 5,133,660 | 7/1992 | Fenick | 433/173 |
| 5,236,359 | 8/1993 | Myers et al. | 433/215 |
| 5,320,529 | 6/1994 | Pompa | 433/215 |
| 5,556,278 | 9/1996 | Meitner | 433/75 |

*Primary Examiner*—Cary E. O'Connor
*Attorney, Agent, or Firm*—Workman, Nydegger & Seeley

[57] ABSTRACT

A method for guiding a surgical drill in a desired direction comprises forming a splint contoured to an area where drilling is desired, disposing a guide means through the splint, aligning the guide means with an alignment means, and disposing the drill through the guide means.

16 Claims, 5 Drawing Sheets

DRILL GUIDE KIT

BACKGROUND OF THE INVENTION

1. The Field of the Invention

This invention relates to surgical drilling applications, and more particularly, to drilling applications involving oral surgery.

2. The Relevant Technology

Drill guides are used to guide a drill in a properly aligned direction. Particularly in the field of surgery, it is vital to drill with accuracy. Serious injury can be caused by drilling at the wrong location or at the wrong angle. In oral surgery, improper drilling can result in misalignment of implanted devices, which can seriously hamper a practitioner's ability to repair a patient's dentition.

In order to place a crown or other device in a patient's jaw, a practitioner is often required to mount an implant within the jaw, then attach the crown or device to the implant. When mounting an implant, a practitioner must accurately drill within the patient's jaw, then place the implant in the drilled area. Before drilling the practitioner may create a splint or retainer-like device which corresponds to the contours of the patient's jaw and contains holes corresponding to the area in the patient's mouth where drilling is desired. The splint is then placed over the patient's jaw and a drill is disposed through the hole into the area in the patient's jaw where drilling is desired.

The contoured splint may succeed in properly orienting the initial location of the drill. However a splint having merely a hole where drilling is desired is not axially aligned. As a result, the drill may begin in the proper location, yet drill at an improper angle of alignment. Improperly aligned drilling results in the improper alignment of an implant which in turn causes improperly aligned crowns, or may even prevent the practitioner from mounting a crown. Improper alignment of implants may require patient's to endure a redrilling and re-implantation of the implant.

Particularly when a plurality of implants are mounted in a patient's jaw, the misalignment of the implants makes it difficult to place crowns on the implants. Many multiple-tooth crowns must be mounted on multiple implants. A multiple-tooth crown may not fit onto one or more implants if any of the implants are misaligned in relation to the others, requiring redrilling of the implant or creative reconfiguration of the crown.

An additional factor compounds the misalignment which may occur when the drill diverges from a desired course. Surfaces within the jaw cause drill bits to drift. Splints merely having holes displaced therethrough are particularly susceptible to having the edge of the hole shaved off by a misguided or drifting drill, resulting in expansion and deformation of the hole. When the hole in the splint is deformed, it allows the surgical drill to vary greatly from the path intended. Previous splints are particularly susceptible to shaving off because they are typically made of acrylic material which is easily cut by drill bits.

SUMMARY AND OBJECTS OF THE INVENTION

It is therefore an object of this invention to make and use a drill guide, splint and drill guide alignment means which can be used to ensure the proper alignment of a drill.

It is a further object of the invention to create a drill guide alignment means which can be used to axially align the drill guide prior to disposition of the drill bit therethrough.

It is a further object of the invention to create a drill guide which can be used to prevent a drill from shaving off and deforming a splint.

It is a further object of the invention to create a drill guide having a course and/or uneven outer surface so that it can be readily connected within a splint.

It is a further object of the invention to create multiple drill guides and corresponding alignment means and to create a system for aligning multiple drill guides in relation to each other.

It is a further object to employ wax in the alignment and cementation of drill guides such that the wax serves to retain the drill guide in proper axial alignment.

It is a further object of the invention to create a kit which can be used to fulfill all of the needs of the practitioner in creating a splint having aligned drill guides in preparation for drilling.

It is a further object of the invention to create and use a drill guide having a corresponding axial alignment mechanism which can be used in a variety of drilling applications, including, without limitation, dentistry, oral surgery, facial surgery, general surgery, back surgery or a variety of other surgical and general drilling applications.

In accordance with these objects, a method for guiding a drill in a desired direction is disclosed, comprising forming a splint contoured to an area where drilling is desired, disposing a guide means through the splint, aligning the guide means with an alignment means, and disposing the drill through the guide means. By placing the alignment means within the guide means and rotating the alignment means, the guide means can be properly aligned within the splint. After the guide means has been aligned within the splint, the practitioner can dispose a drill through the guide means and thereby drill into a patient's jaw with a properly aligned drill, resulting in properly aligned implants and crowns.

The foregoing objects and features of the present invention, as well as other objects and features of the present invention, will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENT

In order to guide a drill in a desired direction, a practitioner forms a splint 10 contoured to an area where drilling is desired, disposes a guide means 12 through the splint 10, aligns the guide means 12 with an alignment means 14, then disposes the drill through the guide means 12. The presently preferred guide means 12 is a cylindrical metal sleeve 12 which is disposed through a splint 10. The alignment means 14 preferably comprises an elongated cylindrical dowel 14. By placing the dowel 14 within the sleeve 12 and rotating the dowel 14, the sleeve 12 can be properly aligned within the splint 10.

In the field of oral surgery, the splint 10 is preferably closely adapted to a patient's remaining teeth, palatal and ridge contours. This close adaption and fit of the splint 10 ensures that it fits reproducibly in one position each time it is removed and replaced within a patient's mouth, and on a model 16 of the patient's dentition, ensuring that drilling occurs in the proper area.

Figure 1:
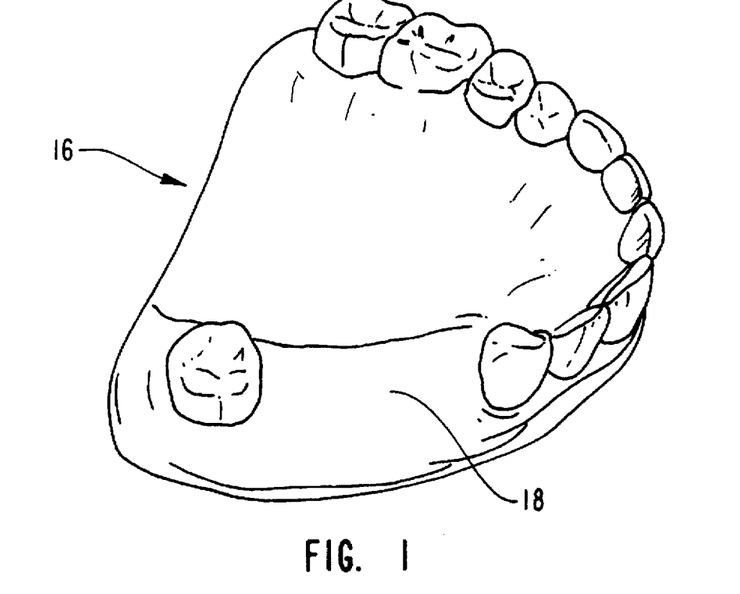
FIG. 1 is a perspective view of a model which is taken of a patient's dentition before creating a splint.

In order to form such a properly contoured splint 10, a model 16 is made of a patient's dentition. As shown in FIG. 1, the model 16 of the patient's dentition typically has an edentulous region 18 corresponding to an edentulous region within the patient's dentition. The edentulous region 18 may comprise one missing tooth, a variety of missing teeth or conceivably an entire jaw of missing teeth. The model 16 is preferably marked in an area where the placement of implants is desired. Preferably, the model 16 is marked by a practitioner: (1) at a point corresponding to the point of desired drilling within the mouth; and (2) in an area corresponding to the shape of the desired splint.

Figure 2:
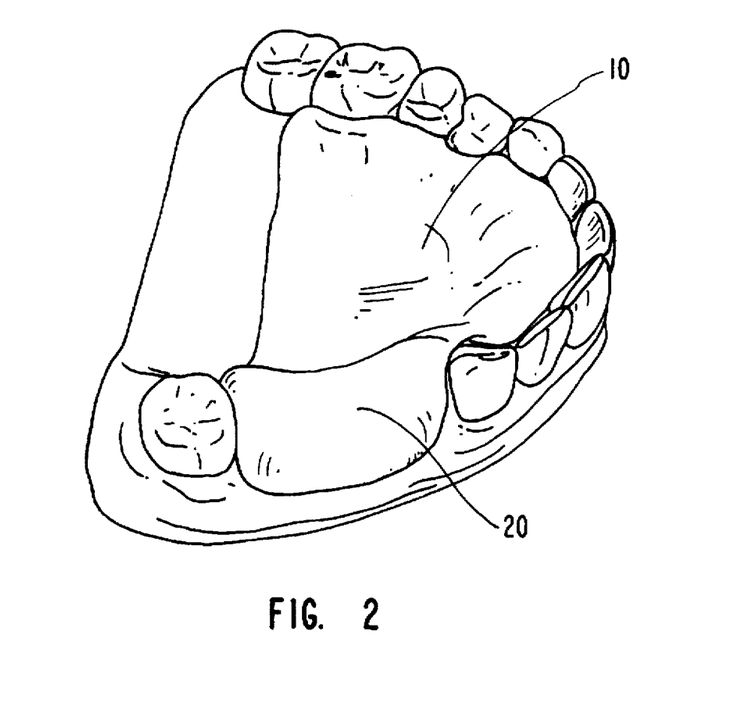
FIG. 2 is a perspective view of the dentition model overlaid by a splint.

Turning to FIG. 2, after the model 16 is formed, a cementitous composition is molded to the contours of the model 16, forming a splint 10. As shown in FIG. 2, the splint 10 is formed such that a tab 20 of the splint 10 covers the edentulous region 18.

Figure 3:
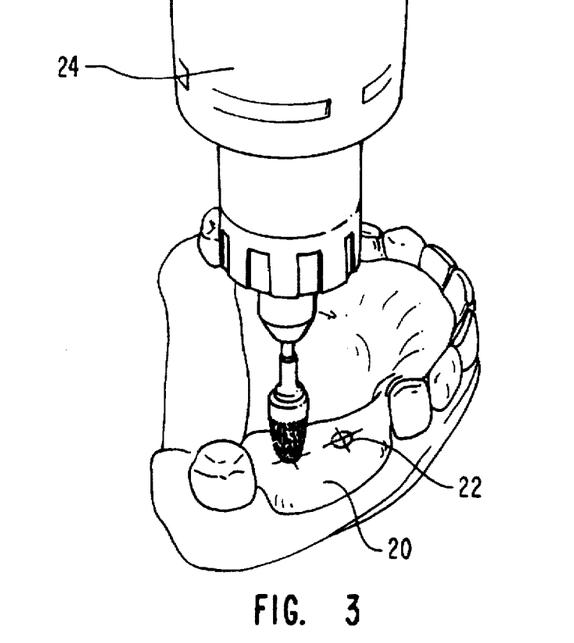
FIG. 3 demonstrates the drilling of a hole in the splint.
Figure 4:
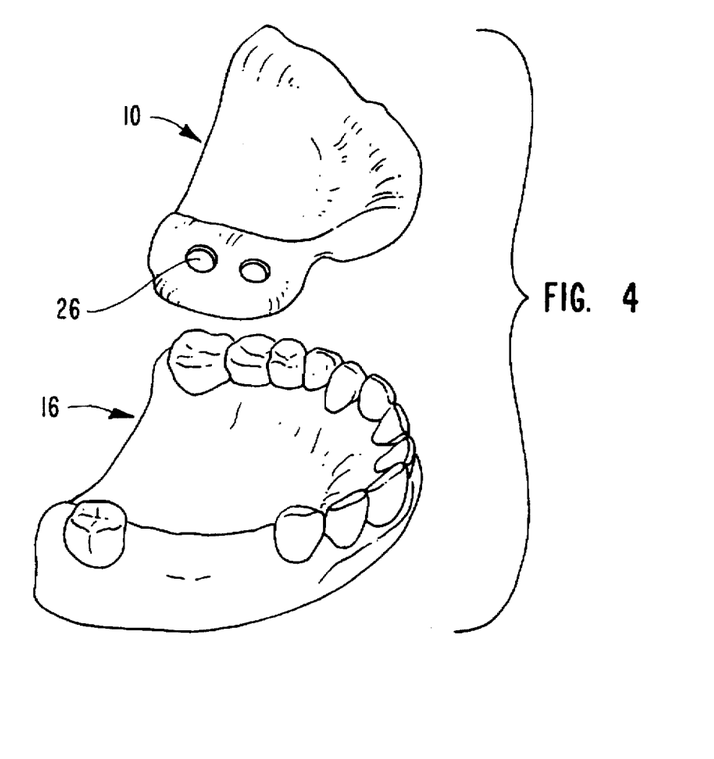
FIG. 4 demonstrates that the splint corresponds to the contours of the dentition model and may have a plurality of holes when a plurality of implants are desired.

Turning to FIG. 3, after the splint 10 is formed, the tab 20 of the splint 10 is preferably marked at an area 22 corresponding to the location within the patient's mouth where drilling is desired. A drill 24 can be used to drill at least one hole 26 in the marked area 22. The at least one hole 26 within the splint 10 is preferably slightly larger than the sleeve 12 to be placed in the hole 26. This is provided so that the sleeve 12 may be properly rotated and aligned within the splint 10. A second hole 26 can also be drilled, resulting in the splint 10 shown in FIG. 4.

It is possible to place a sleeve 12 in the desired area of the splint 10 while the splint 10 is drying, avoiding the step of drilling a hole 26 through the splint 10 after the splint 10 has dried. The sleeve 12 may be placed in the desired area through press fitting, for example.

Figure 5:
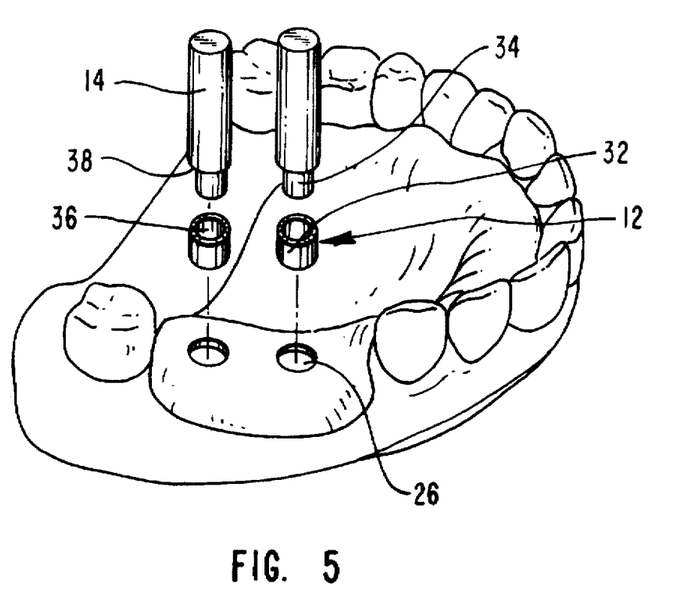
FIG. 5 is an exploded view demonstrating the placement of sleeves into a splint and the placement of a plurality of dowels within the sleeves in order to align the sleeves.
Figure 6:
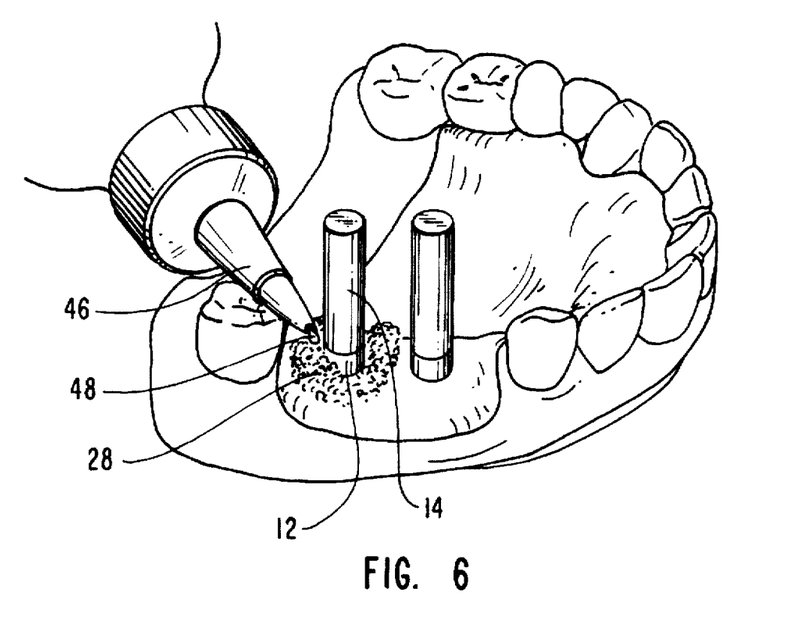
FIG. 6 demonstrates the cementation of sleeves into a tab of a splint.

Preferably, a practitioner allows the splint 10 to dry or set, then forms at least one hole 26 in the splint 10. The practitioner then press fits at least one sleeve 12 into the at least the one hole 26, as shown in FIG. 5, and cements the sleeve 12 within the splint 10, using additional cementitous composition 28, as shown in FIG. 6. The practitioner may press fit a plurality of sleeves 12 into a corresponding holes 26.

Either before the additional cementitous composition 28 is deposited between the sleeve 12 and the splint 10, or at least before the additional cementitous composition 28 dries, a dowel 14 for alignment of the sleeve 12 is inserted into the sleeve 12 and rotated, properly aligning the sleeve 12 according to the angle in which drilling is desired. As the additional cementitous composition 28 dries, the dowel 14 can be manipulated to precisely align the sleeve.

After the additional cementitous composition 28 dries, a drill may be disposed through the aligned sleeve 12 and drilling may occur at a desired location in the desired alignment.

However, after the dowel 14 and its corresponding sleeve 12 are aligned, yet before the additional cementitous composition 28 is added, wax 30 is preferably placed on a dowel 14 and on another surface so that the dowel 14 and its corresponding sleeve 12 are held in place while the additional cementitous composition 28 is added and dries. It is also possible to add the wax after the additional cementitous composition 28 has been added, but before it dries.

Figure 7:
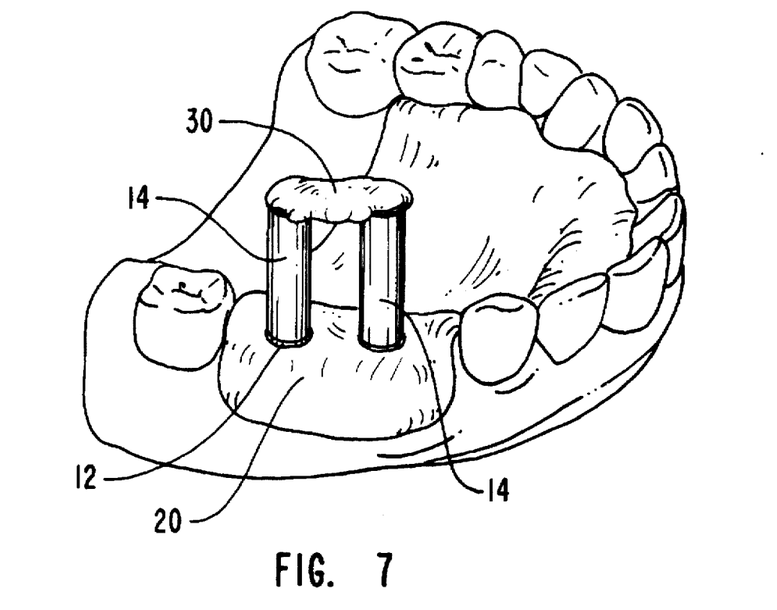
FIG. 7 demonstrates the placement of wax onto a plurality of dowels while the cementitous composition connecting the sleeves to the splint dries, thus holding the dowels, and as a result, their corresponding sleeves, in alignment with each other.

Turning to FIG. 7, it is possible to place wax 30 on the top of a number of dowels 14 when a plurality of dowels 14 are used, such as when it is desired to drill two holes in a patient's mouth. This placement of wax 30 ensures that the plurality of sleeves 12 are aligned in relation to each other.

Wax 30 may also be placed between one or more dowels 14 and the splint 10 or between one or more dowels 14 and the model 16 to retain a single dowel 14 or even a plurality of dowels 14 in proper alignment while the additional cementitous composition 28 dries.

After the additional cementitous composition 28 dries, the wax 30 and the dowel 14 may be removed. It is also possible to remove the dowel or dowels after alignment, but before drying. It is preferable after drying has occurred to recheck the alignment of the sleeves 12 using the dowels 14 (by replacing the dowels 14 if they have been removed). Also after the additional cementitous composition 28 has dried, it is preferable to exert pressure against the dowels 14 within the sleeves 12 to ensure that the sleeves 12 are not loose or will not be easily displaced. Finally, it is preferred to pass and rotate a surgical drill or other similar object through the sleeve 12 to check for binding or debris before drilling is commenced.

Figure 8:
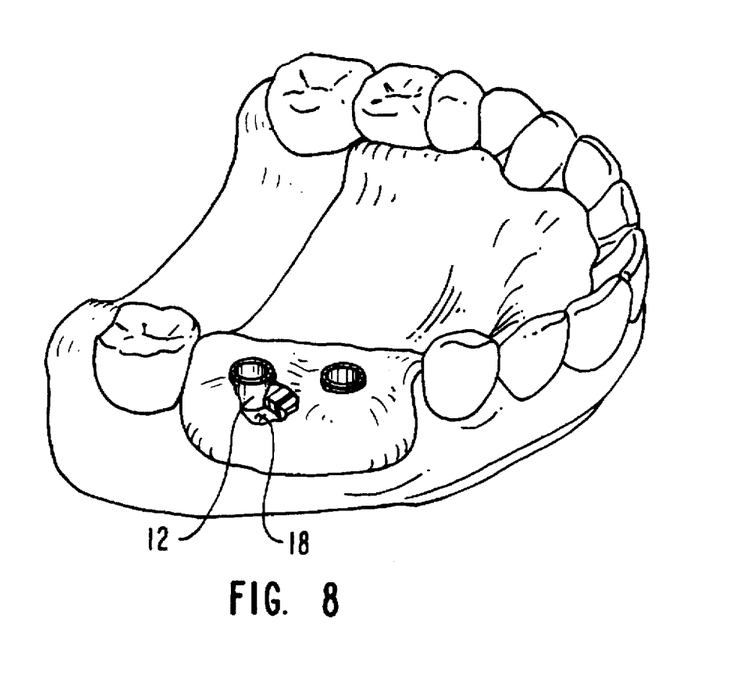
FIG. 8 is a cut away view of the sleeve within the splint demonstrating that, in the preferred embodiment, the sleeve is in contact with an edentulous region of the dentition model while being cemented within the splint so that the sleeve will be in contact with the patient's edentulous region when the splint is placed in the patient's mouth.

FIG. 8 demonstrates that the addition of the additional cementitous composition 28 preferably builds up the tab 20 of the splint 10 such that the outer surface 32 of the sleeves 12 are surrounded by the resulting splint 10. The original cementitous composition which is used to create the splint is preferably the same composition as the additional cementitous composition 28 which is used to connect the sleeve 12 to the splint 10. FIG. 8 also demonstrates that the sleeve 12 is preferably disposed onto the edentulous region 18 of the model 16 and will preferably be disposed directly onto the patient's edentulous region, ensuring that the drill is properly aligned as it contacts the patient's edentulous region.

Figure 9:
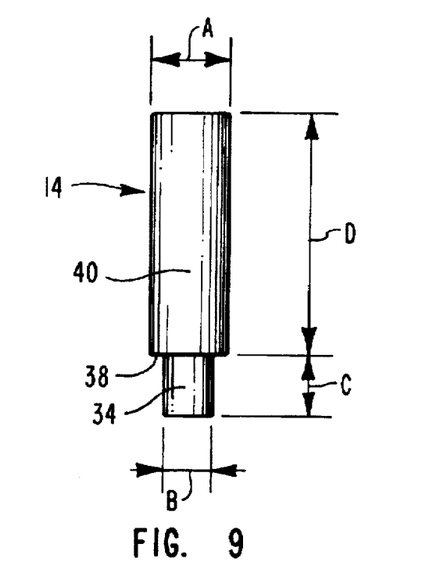
FIG. 9 is a view of a dowel.

FIG. 9 shows a view of the preferred dowel. When a sleeve 12 is aligned, a neck 34 of the dowel 14 is disposed through the inner surface 36 of the sleeve 12, as shown in FIG. 5. The neck 34 slides into the sleeve 12 until the shoulder 38 of the dowel 14 interfaces the sleeve 12. The body 40 of the dowel 14, which remains outside the sleeve 12, can be oriented and by so orienting the body 40, the sleeve 12 is oriented.

For a drill bit having a diameter of about 0.138±0.001 inches, the distance A is preferably 0.187±0.001 inches; the distance B is preferably 0.142±0.001 inches; the distance C is preferably 0.157±0.001 inches; and the distance D is preferably 1 inch. The preferred corresponding sleeve has an inner diameter of 0.144±0.001 inches, corresponding somewhat to the diameter of the neck 34 of the dowel, while the sleeve has an outer diameter of 0.187±0.001 inches.

Each of these distances depends upon the particular sleeve which is used. A variety of sizes are available depending upon the drill and drill bit which are chosen.

The sleeve 12 preferably has an outer surface 32 having a rough or uneven texture so that the additional cementitous composition 28 surrounding the sleeve 12 attaches more readily to the sleeve 12. This texture can be achieved through sandblasting, or glass bead blasting, for example. A rough shape, such as an X, or a series thereof, may also be chiseled into the outer surface 32 of the sleeve 12. The sleeve 12 is preferably made of metal, for example, stainless steel (such as 316 stainless steel) or a variety of other materials which are known in the art which can withstand the dramatic forces of drills.

One skilled in the art will recognize that the dowel 14 represents an alignment means which can have a variety of shapes and sizes depending on the circumstances and that the corresponding sleeve represents a guide means or drill guide which can have a variety of shapes and sizes depending upon the particular drilling application involved.

Figure 10:
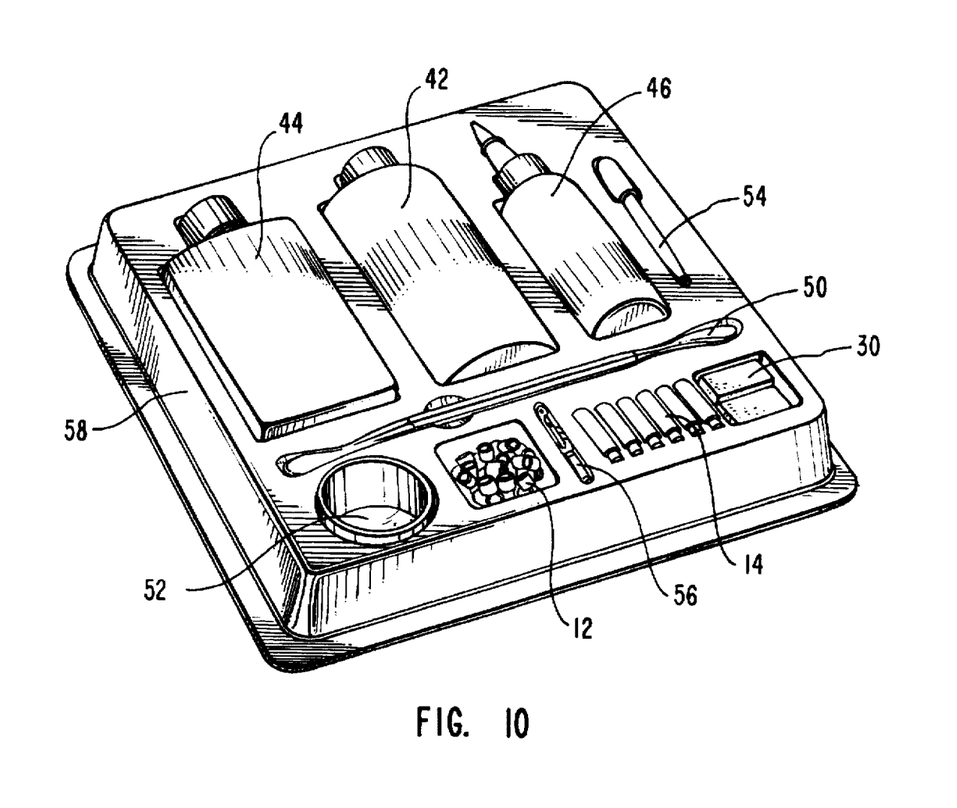
FIG. 10 demonstrates the components of the preferred drill guide kit collected together in a container.

Turning to FIG. 10, it is preferred to use a kit having all of the necessary elements for creating a properly aligned splint. At least one sleeve 12 and preferably a variety of sleeves 12 are provided within the kit as well as differently sized and shaped dowels 14. In addition to the at least one sleeve 12 and at least one dowel 14, the kit includes a cementitous composition from which a splint 10 can be formed. Additional components are included in the preferred embodiment.

Preferably, to form the cementitous composition, a resinous material, such as powder and liquid acrylic cement are mixed. The most preferred cementitous composition is comprised of compounded methyl methacrylate polymer (a powder) and compounded, inhibited methyl methacrylate monomer (a liquid), which are combined to form the cementitous composition.

The cylindrical container 42 disclosed in FIG. 10 can be used to retain the liquid portion of the most preferred cementitous composition, but a variety of other containers could also be used for this purpose. Similarly, a variety of containers can be used to contain the powder portion. One bulk container 44 could be used to hold powder. Another dropper powder container 46 can be used to contain the same kind of powder 48 as contained in the bulk container 44 and is conveniently used to apply the powder 48 between the already formed splint 10 and the sleeve 12, as shown in FIG. 6. A spatula 50 is provided for removing powder from the bulk powder container 44 and placing it in a mixing bowl 52 and for stirring the powder and liquid in the bowl 52 when creating the splint 10.

A dropper 54 may be used to apply liquid into the mixing bowl 52 when creating the splint 10 and/or onto the powder 48 placed between the sleeve 12 and the splint 10 to form the additional cementitous composition 28 in FIG. 6. Optionally, powder and liquid can be mixed in the mixing bowl 52 or another structure and applied to the splint 10 as additional cementitous composition 28.

Wax 30 is also provided for ready use in stabilizing the dowel 14 during the addition and/or drying of the additional cementitous material 28 in the manner described above. A drill bit 56 or a plurality thereof may be included in the kit. The container 58 for these instruments preferably has contours such that the instrument will readily fit within the container. The kit can be marketed as a complete kit for creating a properly aligned drill guide and splint combination.

In addition to using the foregoing technology relating to the creation of properly aligned dental splints, the technology may be used in a variety of circumstances in which properly aligned drilling is desired. The applications may be of particular use in a variety of surgical procedures. For example, a splint may be created corresponding to an ear or a nose which can be used to place an implant into an area surrounding the ear or the nose onto which a prosthetic may be placed or which may be used in the surgery or repair of the appendage. The technology also has a wide variety of uses in nonsurgical applications where properly aligned drilling is critical. The splint can be used in any drilling application in which the sleeve can be adjusted within and retained within a composition, object, machine, article of manufacture, device or other retaining means.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for guiding a drill in a desired direction in a patient's mouth, comprising:
   forming a splint contoured to fit the patient's dentition, the splint having a first hole corresponding to an area in the dentition in which drilling is desired;
   press fitting a first guide means into the first hole;
   inserting a first alignment means partially inside the first guide means for alignment of the first guide means;
   rotating the first alignment means such that the first guide means is aligned to guide the drill in a desired direction;
   removing the first alignment means; and
   disposing the drill through the aligned first guide means.

2. A method as in claim 1, wherein the press fitting step comprises press fitting a cylindrical metal sleeve into the first hole.

3. A method as in claim 1, wherein the press fitting step further comprises the step of orienting the first guide means such that it is adapted to rest upon a patient's edentulous religion when the split is placed within the patient's mouth.

4. A method as in claim 1, wherein the inserting step comprises inserting a portion of an elongated cylindrical dowel into the first guide means.

5. A method as in claim 1, further comprising the step of deposition a cementitous composition between the first guide means and the splint and allowing the cementitous composition to dry.

6. A method as in claim 5, wherein the depositing step occurs after the rotating step.

7. A method as in claim 5, further comprising the step of supporting the first alignment means by placing a wax between the first alignment means and the splint to retain the first guide means in proper alignment while the cementitous composition dries.

8. A method as in claim 7, wherein the step of placing said wax between the first alignment means and the splint occurs before the depositing step.

9. A method as in claim 1, wherein the splint has a second hole corresponding to an area in the dentition in which drilling is desired and further comprising:

press fitting a second guide means into the second hole;

inserting a second alignment means partially inside the second guide means for alignment of the second guide means;

rotating the second alignment means such that the second guide means is aligned to guide the drill in a desired direction;

depositing a cementitous composition between the first guide means and the splint and between the second guide means and the splint;

allowing the cementitous composition to dry;

removing the second alignment means; and disposing the drill through the aligned second guide means.

10. A method as in claim 9, further comprising the step of supporting the first and second alignment means by placing a wax between the first and second alignment means to retain the first and second guide means in alignment while the cementitous composition is deposited and dries.

11. A method for guiding a drill in a desired direction in a patient's mouth, comprising:

forming a splint contoured to fit the patient's dentition, the splint having a hole corresponding to an area in the dentition in which drilling is desired;

placing a cylindrical sleeve having a rough outer surface into the hole such that the sleeve is adapted to rest upon a patient's edentulous region when the splint is placed within the patient's mouth;

inserting a neck of a cylindrical dowel inside the sleeve until a shoulder of the dowel interfaces the sleeve;

rotating the dowel such that the sleeve is aligned to guide the drill in a desired direction;

depositing a cementitous composition between the sleeve and the splint;

allowing the cementitous composition to dry;

removing the dowel; and disposing the drill through the aligned sleeve.

12. A method for preparing a splint used in guiding a drill in a desired direction in a patient's mouth, the splint contoured to fit a patient's dentition, comprising:

forming a splint by molding a first cementitous composition to the contours of an area where drilling is desired;

disposing a guide means through the composition;

aligning the guide means with an alignment means;

depositing a second cementitous composition between the guide means and the splint;

allowing the cementitous compositions to dry; and removing the alignment means.

13. A method as in claim 12, wherein the splint is formed from a cementitous composition and the guide means is disposed through the cementitous composition before the cementitous composition dries into a splint.

14. A dental kit for guiding a drill in a desired direction through a splint adapted for use in a patient's mouth, the kit comprising:

a cementitous composition from which a splint is formed;

a plurality of cylindrical sleeves for placement within the splint whereby the drill is guided through at least one of the sleeves; and a plurality of dowels, each dowel having a first portion which will permit a friction fit of the first portion within a sleeve, and each dowel having a second alignment portion which has a length so that when the dowel is inserted into a corresponding sleeve, the alignment portion will extend beyond the sleeve's length by at least several times to permit visual inspection for purposes of axially aligning each dowel with any adjacent dowel and sleeve combination, thereby permitting each sleeve placed within the splint to be axially aligned prior to final cementing of the sleeves within the splint.

15. A kit as in claim 14, wherein each dowel is comprised of:

a body;

a shoulder at one end of the body; and a neck extending from the shoulder;

the dowel designed such that the neck slides into the guide means until the shoulder interfaces the guide means.

16. A kit as in claim 14 wherein the cementitous composition is comprised of a liquid and a powder component and further comprising:

a spatula for mixing the powder and liquid components;

a mixing bowl wherein the powder and liquid components are mixed;

a dropper for adding the liquid to the powder;

a container for containing the liquid;

at least one container for containing the powder;

a wax for retaining the guide means in alignment while the cementitous composition dries; and at least one drill bit.

* * * * *

UNITED STATES PATENT AND TRADEMARK OFFICE
CERTIFICATE OF CORRECTION

PATENT NO. : 5,718,579
DATED : Feb. 17, 1998
INVENTOR(S) : Brent D. Kennedy

It is certified that error appears in the above-identified patent and that said Letters Patent is hereby corrected as shown below:

Col. 6, line 60, before "when" change "religion" to --region--

Col. 6, line 60, before "is" change "split" to --splint--

Col. 6, line 65, before "a" change "deposition" to --depositing--

Signed and Sealed this

Twenty-ninth Day of December, 1998

*Attest:*

BRUCE LEHMAN

*Attesting Officer*         *Commissioner of Patents and Trademarks*